United States Patent [19]

Denard

[11] 4,387,726
[45] Jun. 14, 1983

[54] DISPOSABLE URINE COLLECTION DEVICE FOR HUMAN MALES

[76] Inventor: Ruthie Denard, 74 Garfield, Detroit, Mich. 48201

[21] Appl. No.: 274,879

[22] Filed: Jun. 18, 1981

[51] Int. Cl.³ .............................................. A61F 5/44
[52] U.S. Cl. .................................. 128/760; 128/771; 604/349; 604/350; 604/353
[58] Field of Search .............................. 128/760–762, 128/1 R, 79, 294–295

[56] References Cited

U.S. PATENT DOCUMENTS

| | | | |
|---|---|---|---|
| 1,228,452 | 6/1917 | Lawrence | 128/295 |
| 2,310,505 | 2/1943 | Blackburn et al. | 128/295 |
| 3,559,651 | 2/1971 | Moso | 128/295 |
| 4,106,490 | 8/1978 | Spilman et al. | 128/295 |

FOREIGN PATENT DOCUMENTS

| | | | |
|---|---|---|---|
| 120453 | 5/1901 | Fed. Rep. of Germany | 128/294 |
| 575307 | 7/1924 | France | 128/294 |

Primary Examiner—George F. Lesmes
Assistant Examiner—Nancy A. B. Swisher
Attorney, Agent, or Firm—Cullen, Sloman, Cantor, Grauer, Scott & Rutherford

[57] ABSTRACT

The disposable urine collection device is concisely constructed for incontinence of urine in the human male. For a male who has problems with the urinary tract, the device is designed to keep the individual clean, dry and comfortable so that he may function to his full capacity without restraint. It consists of a combined pubic arch support and waist belt adapted to fit and be worn around the waist and the lower part of the male abdomen. It also includes a combined scrotal support and belt which is adapted to extend around the buttock of the user, with the last mentioned belt having on one end thereof means for removably connecting same to the waist belt. A urine collecting structure is carried by, secured to and depends from the arch support and includes an inner container or cylinder into which the penis is adapted to extend and an outer container or cylinder into which the inner container extends. The outer container has a length greater than the length of the inner container whereby when the device is in use the urine discharged from the penis will drain through a small opening provided in the bottom of the inner container which collects and stores the urine. The double cylinder container or structure thus described is six to eight inches in length and is made of soft, strong, durable, flesh-like medically approved vinyl plastic material which is comfortable to wear and functions as an under garment. It holds 150 cubic centimeters or more of urine without discomfort.

11 Claims, 6 Drawing Figures

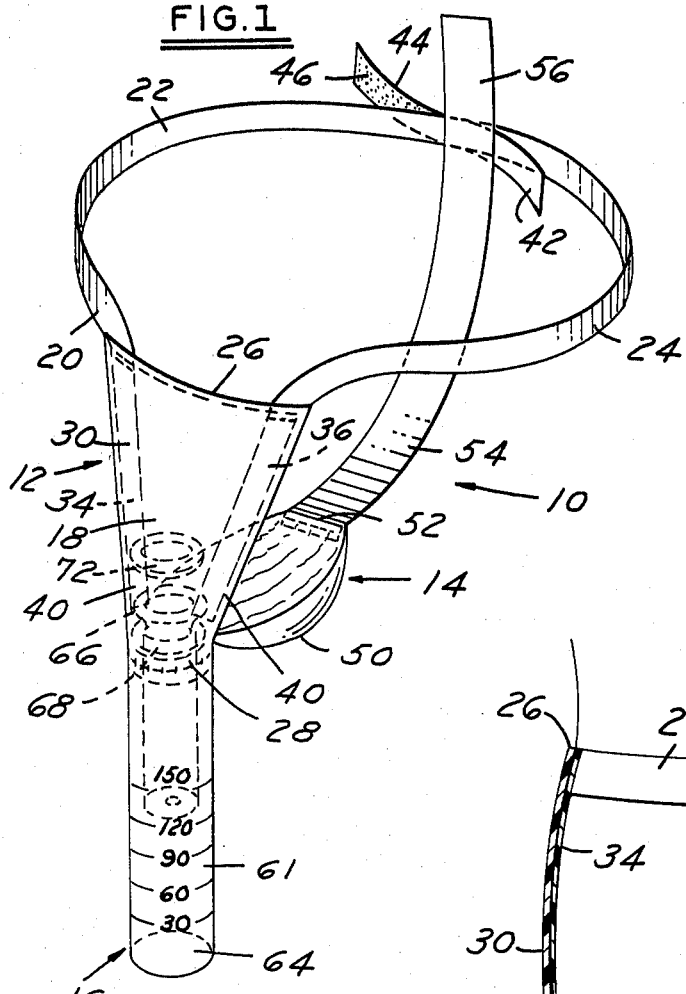
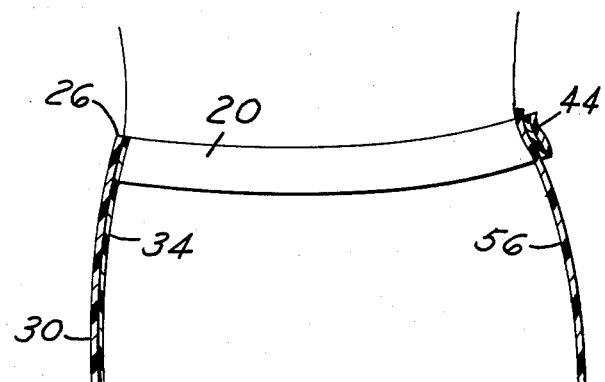
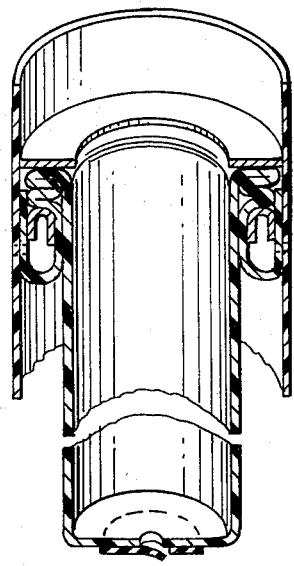
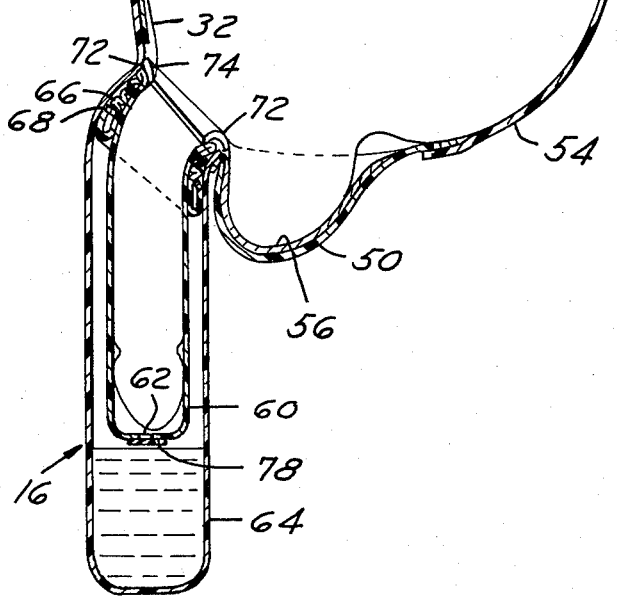

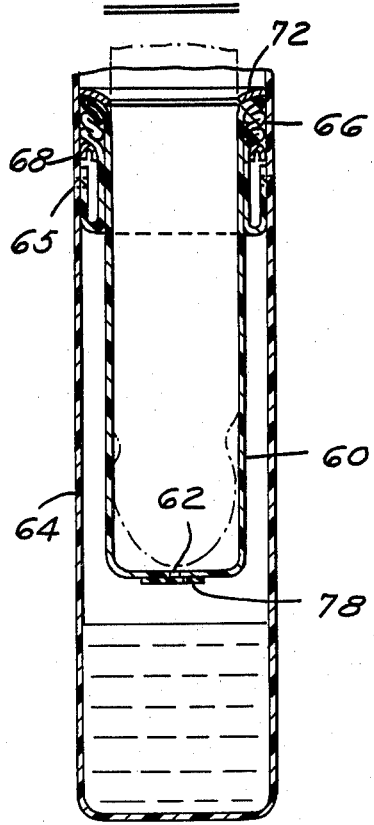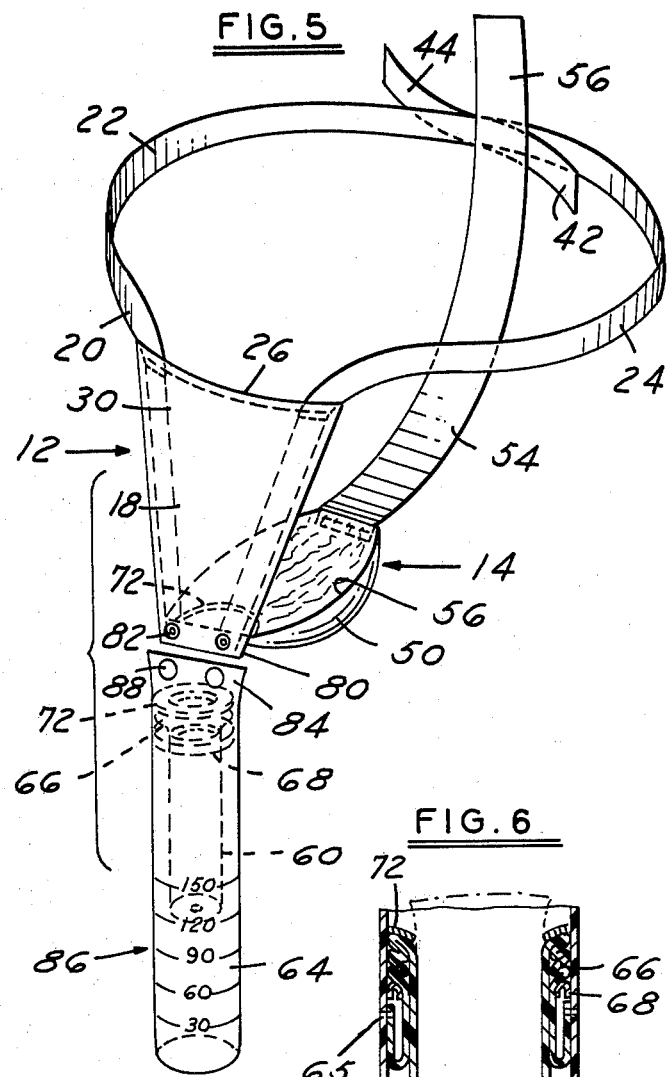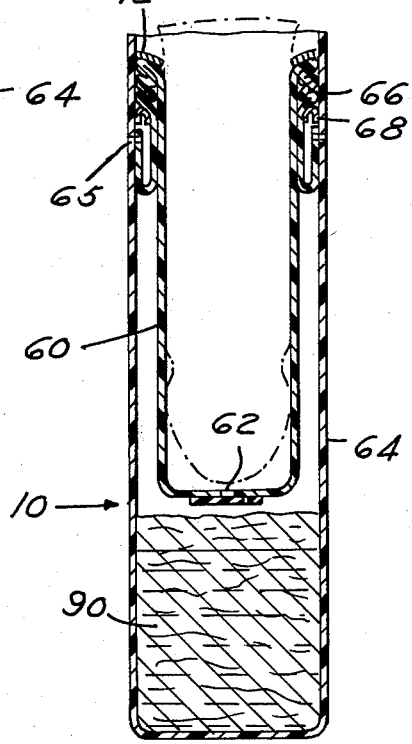

DISPOSABLE URINE COLLECTION DEVICE FOR HUMAN MALES

BACKGROUND OF THE INVENTION

1. Field of the Invention

The present invention pertains to urine collection devices for human males. Such devices are needed not only by incontinent male individuals but also by those who, by virtue of their particular circumstances, are precluded from using ordinary rest room facilities for either short or extended periods of time. Examples are those who are geriatric males, chronically ill or are undergoing post-operative treatment in bed. Others are males who are otherwise incapacitated, disoriented or have a continuous drip as well as those whose occupations demand that they remain on duty and/or continuously wear special protective clothing for extended periods of time. Regardless of the cause of the urinary problem, such condition may present emotional, social and psychological problems in the human male.

In providing a urine collection device for human males, several particular problems must be considered. One of these is to provide the male with the most positive protection possible against leakage of urine from the collection device. At the same time, it is necessary to limit the contact of urine with the exterior of the male's penis to the greatest extent possible, both in terms of surface area and the length of contact time. Thus, it is necessary that the urine be carried away from the penis area quickly and completely. Further, it is necessary that the urine collection device be sanitary as well as disposable and designed to keep the individual clean, dry and comfortable so that he may function to his full capability without restraint. Thus, a person having urinary problems may help maintain satisfactory emotional response in the event of the passing of urine. With such device, the person may enjoy almost any activity while engaged in work, play, motoring, or even exercising such as jogging.

2. Description of the Prior Art

Urine collection devices are known for males as well as for females. Disposable urethra catheter assemblies have been suggested heretofore and two examples of the prior art are shown in U.S. Pat. No. 4,246,901 entitled "Urine Collection Device", Inventors, Robert A. Frosch et al. and in U.S. Pat. No. 4,246,909 entitled "Disposable Urethra Catheter Assembly", Inventors Yeongchi Wu et al., each patent dated Jan. 27, 1981. In addition, the prior art devices known to Applicant for use by males are not comfortable and leakage occurs, all of which interferes with the user's freedom of movement and ability to assume various postures. Such devices also limit his choice of clothing. Thus the prior art devices known to applicant are susceptible to leakage and cause considerable discomfort due to being in contact with the sensitive scrotal area. Another problem of the prior art is catherization. This is extremely irritating and obviously unsuitable for long term use for men who otherwise are healthy and active or for one whose activities are restricted due to occupational or like circumstances. Thus, the problems of males are both numerous and serious and not the least of these problems are those created by conventional urine collection apparatuses.

SUMMARY OF THE INVENTION

The present invention provides a disposable urine collection device for human males which permits the human male to function to his full capabilities without restraint and is particularly ideal for the male who has problems with the urinary tract regardless of the cause. Thus, the present invention is designed to assist in the elimination of certain social, emotional and psychological problems and to help the male person maintain satisfactory emotional response and to possibly gain some control through habit training.

Thus, it is a feature of the present invention to provide a disposable urine collection device for human males comprising a combined pubic arch support and belt adapted to fit and be worn around the waist and the lower part of the male abdomen including an arch support for covering the pubic area. The belt includes a pair of strands having end portions secured to the arch support and to the upper end thereof. The other end portions of the strands include fastening means for removably securing the strands together around the waist of the user.

It is a further feature of the present invention to provide a disposable urine collection device of the aforementioned type which includes a combined scrotal support and belt including an open scrotal support secured to the arch support, with the scrotal belt adapted to extend around the buttocks of the user. The scrotal belt has on the free end thereof means for removably securing it to the waist belt.

A still further feature of the present invention is to provide a disposable urine collection device for human males of the aforementioned type wherein a urine collecting structure is carried by, secured to and depends from the arch support. The structure includes an inner container or cylinder through which the penis is adapted to extend and an outer container or cylinder into which the inner container extends. The inner container has a relatively small opening in the bottom thereof. The outer cylinder has a length greater than the length of the inner container. When the device is in use, the urine discharged through the penis will drain through the small opening provided in the bottom of the inner container into the outer container which collects and stores the urine. The device is sanitary, disposable and is designed to be changed every four hours or whenever is necessary for human comfort and for a sense of well-being.

Another feature of the present invention is to provide a disposable urine collection device wherein the upper edge portion of the inner container is connected to the upper edge portion of the outer container so as to provide a fluid tight seal adjacent the arch support which prevents leakage from the outer container.

Still another feature of the present invention is to provide a disposable urine collection device wherein a graduated scale is provided on the outer container or cylinder so that the amount of urine collected within the outer container may be readily determined. As an example, the volumetric capacity of the outer container is approximately 150 cubic centimeters or more.

A further feature of the present invention is to provide a disposable urine collection device wherein the strands of the waist belt may be connected around the waist by adhesive fastening means, snap fasteners or a belt and latch device.

A still further feature of the present invention is to provide a disposable urine collection device wherein the combined pubic arch support and belt, the combined scrotal support and the urine collecting structure are made from a medically approved plastic material such as vinyl plastic.

Another feature of the present invention is to provide a disposable urine collection device wherein the scrotal support is provided with a soft fabric material to absorb perspiration and to prevent irritation to the scrotal area of the user.

Still another feature is to provide a disposable urine collection device wherein absorbent material is located at least within the lower portion of the outer container or cylinder for absorbing and retaining the urine discharged therein.

A further feature is to provide a disposable urine collection device wherein the urine collecting structure is secured to the arch support by sewing or stitching or is removably attached thereto by means including male and female snap fasteners.

A still further feature is to provide a disposable urine collection device wherein the bottom of the inner container is provided with a flap valve which prevents the reverse flow of the urine from the outer container into the inner container via the aforementioned small opening.

Another feature is to provide a disposable urine collection device wherein the inner and outer containers are in the form of cylinders, the outer cylinder being closed and sealed throughout its entire extent and the inner cylinder being open at the top and otherwise closed except for the small opening, provided in the bottom thereof.

Still another feature of the present invention is to provide a urine collection device wherein a relatively thin adjustment disc having a center opening is sleeved over the extended and rolled up upper end portion of the inner cylinder to support same and to assist in the adjustment of the length of the inner cylinder to fit the penis.

A further feature of the present invention is to provide a disposable urine collection device wherein a second relatively thin disc is provided with a center opening and is adapted to be placed over the penis prior to the insertion of same into the inner cylinder to provide a cushion or pad for the scrotal area of the user to avoid contact with the rolled up inner end portion of the inner cylinder.

A still further feature of the present invention is to provide a disposable urine collection device wherein the discs employed are identical, with one or both the discs being provided with adhesive or non-skid surfaces for assisting in the adjustment of the inner cylinder and the covering of the rolled up inner end portion of the inner cylinder.

Another feature of the present invention is to provide a disposable urine collection device wherein the arch support comprises two relatively thin plastic panels, with the end portions of the strands extending from the upper edge portion to the lower edge portion of the arch support and being located therebetween and including means for securing the end portions of the strands to the panels.

Finally, it is a feature of the present invention to provide a disposable urine collection device that is concisely constructed for incontinency of urine in the male and is designed to keep the individual clean, dry and comfortable so that he may function to his full capacity without restraint.

BRIEF DESCRIPTION OF THE SEVERAL VIEWS OF THE DRAWINGS

FIG. 1 is a perspective view of the disposable urine collection device forming one embodiment of the present invention;

FIG. 2 is a side elevation of the disposable urine collection device of FIG. 1 mounted on a human male;

FIG. 3 is a fragmentary perspective view showing the manner in which the inner and outer cylinders and the discs of the disposable urine collection device are utilized;

FIG. 4 is a fragmentary side elevational and sectional view through the urine collecting structure and showing parts of the human male;

FIG. 5 is a perspective view similar to the embodiment of FIG. 1 and illustrating the detachable urine collecting structure carried by the arch support of the urine collection device; and FIG. 6 is a fragmentary side elevational and sectional view and showing parts of the human male and an absorbent material contained within the outer cylinder to absorb the urine.

DETAILED DESCRIPTION OF THE PREFERRED EMBODIMENT

The disposable urine collection device for human males is designated by the numeral 10 in FIG. 1. It comprises three main components including a combined pubic arch support and belt 12, a combined scrotal support and belt 14 and a urine collecting structure 16.

The combined pubic arch support and belt 12 is adapted to fit and to be worn around the waist in the lower part of the human abdomen and buttocks as illustrated in FIG. 2. The combined pubic arch support and belt 12 includes an arch support 18 and a belt 20 including a pair of strands 22 and 24.

The arch support 18 has an upper edge portion 26 and a lower edge portion 28. The arch support 18 is designed to cover the pubic area and comprises two relatively thin plastic panels 30 and 32 (FIG. 2), each panel being in the form of a trapezoid as best shown in FIG. 1. Strand 22 has one end portion 34 located between the panels 30 and 32 while the other strand 24 has one end portion 36 located between the panels 30 and 32. Each end portion 34 and 36 extends from the upper edge portion 26 of the arch support to the lower edge portion 28 thereof. The end portions 34 and 36 and the panels 30 and 32 are stitched along the four edges thereof as indicated by the numeral 40. The peripheral stitching holds the relatively thin panels 30 and 32 closely together. In addition, the stitching holds the end portions 34 and 36 of the strands 22 and 24 in place and provides additional support for the belt 20 when in use.

The other end portions 42 and 44 of the belt strand 22 and 24 respectively include fastening means 46 for removably securing the strands 22, 24 together around the waist of the user as shown in FIG. 2. The fastening means 46 may take one of a number of forms. Preferably, the fastening means 46 is in the form of adhesive provided on the end portions 44, 46 whereby, after the adhesive portions 46 are exposed the other end portions 42, 44 of the strands of the belt 20 are secured together around the waist of the user. Rather than adhesive fastening means 46 provided on the end portions 42, 44, it should be appreciated that the strands 22, 24 may include complementary male and female snap fasteners whereby the strands of the belt 20 may be secured around the waist of the user.

It is another optional feature of the present invention to utilize on one strand 22, 24 a belt buckle and a latch, with the other strand 22, 24 having a series of longitudinally space openings for selectively receiving the latch provided on the other strand thereby removably securing the strands of the belt together around the waist of the user.

The combined scrotal support and belt 14 includes an open scrotal support 50 having one edge secured to the lower edge 28 of the arch support 18 and with the other edge 52 being connected to one end of the belt or strap 54 which is adapted to extend around the buttocks of the user. The belt or strap 54 has on the other end 56 means such as adhesive means for removably connecting same to the first mentioned belt 20 as best illustrated in FIGS. 1 and 2. The scrotal support 50 is made from a relatively thin plastic material and has on the inner surface thereof a fibrous cushion or pad 56 which is connected along the longitudinal edges thereof to the plastic scrotal support 50. The purpose of the soft fabric material 56 is to provide means for absorbing perspiration in the adjacent area and for preventing irritation to the scrotal area of the user as illustrated in FIG. 2.

The urine collecting structure 16 is carried by, is secured to, and depends from the lower edge 28 of the arch support 18 as best illustrated in FIGS. 1 and 2. The structure 16 includes an inner container or cylinder 60 into which the penis is adapted to extend. The inner container 60 has a relatively small opening 62 in the bottom thereof. The inner cylinder 60 extends into the outer container or cylinder 64 which has on the outer surface thereof a graduated scale 61 in centimeters (FIG. 1) so that the amount of urine collected within the outer container 64 may be readily determined. The outer cylinder or container 64 has a length greater than the length of the inner container 60 whereby when the device 10 is in use, the urine discharged through the penis will drain through the small opening 62 provided in the inner cylinder 60 into the outer container or cylinder 64 which collects and stores the urine as best shown in FIG. 2. The volumetric capacity of the outer container 64 is approximately 150 centimeters or more. This depends, of course, upon the size of a human male, size of container 64 and other factors.

It is anticipated that the device 10 will come in one size and that it is adjustable to fit most human males. Normally, the urine is secreted at the rate of 1-2 milliliter (ml) per minute. The average daily output is 1,000 to 1,500 cubic centimeters every 24 hours. When the bladder contains about 250 centimeters, the pressure stimulus produces the nerve impulse to urinate. In some cases the stimulus or urge is not felt or the pressure stimulus may produce nerve impulse with such urgency, the individual has to urinate immediately. These conditions as noted previously present social and psychological problems. Therefore, it is believed that the present device 10 with the double cylinder structure 16 in which the inner cylinder 60 houses the penis and the outer cylinder 64 receives the urine can hold up to approximately 150 to 200 cubic centimeters of urine depending upon the size of the penis and can do so without discomfort. The device 10 is designed to keep the individual clean, dry and comfortable so that he may function to his full capacity without restraint. The cylinder structure 16 has a length from six inches to eight inches.

The urine collection device 10 may be folded easily to place inside male's coat pocket. It is sanitary and disposable after use. The combined pubic arch support and belt 12, the combined scrotal support and belt 14 and the urine collecting structure 16 are made from a medically approved plastic material such as vinyl plastic. The only non-plastic material utilized is the padded cushion 56 which is made from a soft fabric material as noted previously.

The upper edge portion of the inner container or cylinder 60 is sealingly secured to the upper portion of the outer container 64 so as to provide a fluid tight seal with the arch support 18 thereby preventing leakage from the outer container 64 along the upper edge portion thereof. The fluid tight seal provided between the inner and outer containers or cylinders 60 and 64 is obtained by securing the same together by stitching or sewing as represented by the numeral 65 in FIG. 4. In addition, the urine collecting structure 16 is secured to the arch support 18 by sewing or stitching.

In use, it is necessary to adjust the length of the inner cylinder 60 to fit the length of the penis. Therefore, the user will adjust the length of the inner cylinder 60 by pulling upwardly the upper edge portion of the inner cylinder 60 above the outer cylinder 64 as shown in FIGS. 3 and 4. Thereafter, the exposed end portion of the inner cylinder 64 is rolled over at 66 and thereafter an adjustment disc 68 is placed over the rolled over portion 66. The adjustment disc 68 is placed over the rolled over portion 66 to retain the inner cylinder 60 in the adjusted length. The adjustment disc 68 is made from a thin plastic material having at least one side provided with an adhesive or a non-skid surface 70. The rolled up end 66 of the inner cylinder 64 is cushioned or placed against the skid or adhesive surface 70 of the adjustment disc 68. Prior to the insertion of the penis into the rolled over adjusted inner cylinder 60, another soft disc 72 is placed over the penis. Disc 72 has an upper side 74. Disc 72 overlies the rolled up end 66 of the inner cylinder 60 so as to produce a cushion or pad for the scrotal area of the user to avoid contact with the rolled up end portion 66 of the inner cylinder 64.

Identical relatively thin and flexible discs may be used for the first disc 68 and second disc 72. The first relatively thin disc 68 has a center opening as mentioned previously which is sleeved over the extended and rolled up end portion 66 of the inner cylinder 60 to support same and to assist in the adjustment of the length of the inner cylinder 60 to fit the penis. The second relatively thin disc 72 is also provided with a center opening and is adapted to be placed over the penis prior to the insertion of same into the inner cylinder 60 to provide a cushion or pad for the scrotal area of the user as shown in FIG. 2 to avoid contact with the rolled up end portion 66 of the inner cylinder 64. One or both of the discs 68, 72 is provided with either an adhesive surface or with a non-skid surface to assist in the adjustment of the inner cylinder 60.

The discs 66, 72 are flat, thin, flexible or foldable and donut shaped and are made from a rubber base material appropriately cushioned or designed to prevent irritation. The discs are each approximately 3.5 inches in diameter having a center opening which is approximately 1.375 inches in diameter.

A further feature of the present invention is the provision of a flap valve 78 which is located exteriorly at the bottom of the inner cylinder 60 and prevents reverse flow of the urine from the outer cylinder 64 into the inner cylinder 60 via the small opening 62 as illustrated in FIGS. 2, 3 and 4. Such reverse flow could happen when a person is engaged in active physical activity such as jogging or when the outer cylinder 64 becomes completely filled or the upper surface of the urine rises above the opening 62.

With the device as heretofore described, the inner and outer containers are in the form of cylinders, with the outer cylinder being closed and sealed throughout its extent and the inner cylinder being open at the top for insertion of the penis and otherwise closed except for the small opening 62.

A modification of the present invention is illustrated in FIG. 5 where like numbers have been utilized to designate similar parts as in the earlier embodiment. The combined pubic arch support and belt 12 and the combined scrotal support and belt 14 are identical to the embodiment of FIG. 1. The only important difference is that the lower edge 80 of the arch support 18 is provided with two male snap fasteners 82 which are adapted to removably support the modified urine collecting structure 86 along the upper edge 84. That edge 84 is provided with corresponding female receptacles 88 for receiving the male snap fasteners 82. The modified urine collecting structure 86 serves the same function and purpose as structure 16. With this embodiment the collecting structure 86 may be easily detached from the remaining portions of the disposable urine collection device after use and a new collection structure 86 may be inserted over the penis in the manner heretofore described and secured to the lower edge of the arch support 18. The discs 68 and 72 are also used with this modified structure.

Thus the embodiment of FIG. 5 is generally similar to the structure of FIG. 1 with the exception that the urine collecting structure 86 and the arch support 30 inclines means for removably attaching the urine collecting structure 86 to the arch support 18. Such means may include male and female snap fasteners 82, 84. The female snap fasteners are carried by the urine collecting structure 86 and the male snap fasteners are carried by the arch support 18.

FIG. 6 illustrates the disposable urine collection device 10 wherein an absorbent material 90 such as cotton is located within the lower portion of the outer container 64 for absorbing and retaining the urine. This may be used when the person is engaged in jogging or other sporting events so as to prevent the urine from splashing and making him uncomfortable.

Thus the devices heretofore described can keep a male, clean, dry and comfortable so that he may function as normally as possible thus helping to provide a sense of well-being. The device is made of sort, strong, durable vinyl that is comfortable to wear and in use feels like an under garment. It is foldable, sanitary and disposable. The sticky or adhesive surfaces on the several discs and belts are provided with peel off covers which are removed prior to use.

I claim:

1. A disposable urine collection device for human males comprising:
   (a) a combined pubic arch support and belt adapted to fit and to be worn around the waist and the lower part of the male abdomen and including an arch support for covering the pubic area and a belt, said arch support being in the form of a trapezoid, having upper and lower horizontal edge portions of varying lengths, with the longest length located at the upper edge portion of the support, said arch support including a pair of vertically extending and converging edge portions between said upper and lower horizontal edge portions, said belt including a pair of strands having end portions secured to said arch support and to said upper edge thereof, the other end portions of said strands including fastening means for removably securing the strands together around the waist of the user;
   (b) a combined scrotal support and belt including an opened scrotal support having one edge secured to said arch support, said last mentioned belt being connected on one end to the opposite edge of said scrotal support and adapted to extend the buttock of the user, said last mentioned belt having on the other end thereof means for removably connecting same to said first mentioned belt;
   (c) a urine collecting structure carried by, secured to and depending from said lower edge portion of said arch support, said structure including an inner container into which the penis is adapted to extend, the inner structure having a relatively small opening in the bottom thereof; said structure having an outer container into which said inner container extends, said outer container having a length greater than the length of said inner container whereby when the device is in use the urine discharged through the penis will drain through said small opening into said outer container which collects and stores same; the upper edge portion of said inner container being sealingly secured to the upper edge portion of said outer container to provide a fluid tight seal adjacent said arch support which prevents leakage of urine from said outer container;
   (d) said inner and outer containers being in the form of cylinders, with the outer cylinder being closed and sealed through its entire extent and said inner cylinder being opened at the top and otherwise closed except for said small opening;
   (e) the bottom of said inner container being provided with a flap valve which prevents reverse flow of the urine from the outer container into the inner container via said small opening;
   (f) a first relatively thin adjustment disc having a center opening sleeved over the upper end portion of said inner cylinder to permit the length of said inner cylinder to be adjusted to fit the length of the penis, with the excess length of the inner cylinder at the upper end portion thereof being adjusted and folded upon itself in layers and held in an adjusted position by said first disc;
   (g) and a second relatively thin disc having a center opening and adapted to be placed over the penis prior to the insertion of same into said inner cylinder to provide a cushion or pad for the scrotal area of the user to avoid contact with the folded upper end portion of said inner cylinder; said second disc overlying and contacting the folded upper end portion of said inner cylinder.

2. A disposable urine collection device of claim 1 wherein the other end portions of said strands are provided with adhesive means whereby when the adhesive portions are exposed, said other end portions of the strands of said belt may be secured together around the waist of the user.

3. The disposable urine collection device defined in claim 1 wherein the inner surface of said scrotal support is provided with a soft fabric material which is secured to said scrotal support and provides means for absorbing perspiration in the adjacent area and preventing irritation to the scrotal area of the user.

4. The disposable urine collection device of claim 1 wherein said urine collecting structure and said arch support includes means for removably attaching said urine collecting structure to said arch support.

5. The disposable urine collection device of claim 4 wherein said last mentioned means include male and female snap fasteners.

6. The disposable urine collection device of claim 5 wherein said female snap fasteners are carried by said urine collecting structure and said male snap fasteners are carried by said arch support.

7. The disposable urine collection device of claim 1 wherein said discs are identical.

8. The disposable urine collection device of claim 7 wherein one or both of said discs is provided with an adhesive surface for assisting in said adjustment of said inner cylinder.

9. The disposable urine collection device of claim 7 wherein the upper surface of said first mentioned disc is either provided with an adhesive surface or with a non-skid surface to assist in the adjustment of the inner cylinder.

10. The disposable urine collection device of claim 7 wherein said discs are donut shaped and are made from a rubber base material.

11. The disposable urine collection device of claim 1 wherein said arch support comprises two relatively thin plastic panels with the first mentioned end portions of said strands extending from the upper edge portion to the lower edge portion thereof and being located between said panels; and means for securing said first mentioned end portions of said strands to said panels along the longitudinal edges of the arch support.

* * * * *